United States Patent [19]

Karamian

[11] 4,195,225
[45] * Mar. 25, 1980

[54] METHOD FOR ASSAYING ENDOTOXINS

[76] Inventor: Narbik A. Karamian, Bethesda, Md.

[ * ] Notice: The portion of the term of this patent subsequent to Jun. 6, 1995, has been disclaimed.

[21] Appl. No.: 912,091

[22] Filed: Jun. 2, 1978

Related U.S. Application Data

[63] Continuation-in-part of Ser. No. 745,966, Nov. 29, 1976, Pat. No. 4,093,381.

[51] Int. Cl.$^2$ ............................................. G01J 1/42
[52] U.S. Cl. ................................................ 250/373
[58] Field of Search .......... 250/372, 373, 458, 461 R, 250/461 B, 343; 356/51

[56] References Cited

U.S. PATENT DOCUMENTS

| | | | |
|---|---|---|---|
| 3,327,119 | 6/1967 | Kamentsky | 356/51 |
| 3,944,391 | 3/1976 | Harrls et al. | 195/103.5 R |
| 4,057,724 | 11/1977 | Adrian et al. | 250/343 |
| 4,093,381 | 6/1978 | Karamian | 250/373 X |

Primary Examiner—Davis L. Willis

[57] ABSTRACT

A new convenient and more reliable spectrophotometric method for assaying endotoxins at levels as low as 1 to 5 ppb. Representative members of six different groups of endotoxins, Shigella, *Serratia marcescens*, Salmonella, *Escherichia coli*, Pseudomonas and Porteus. were examined and each exhibited an absorption maxium of 258 to 260 nm.

6 Claims, No Drawings

METHOD FOR ASSAYING ENDOTOXINS

CROSS REFERENCE TO OTHER APPLICATIONS

This application is a continuation in part of application Ser. No. 745,966 filed Nov. 29, 1976 now U.S. Pat. No. 4,093,381.

BACKGROUND OF THE INVENTION

Endotoxins, which are commonly known as pyrogens, are substances produced by microorganisms growing in water or in aqueous solutions. They cause inflammation and general fever when injected intravenously. They are colloidal in nature and they persist even after the organisms which produce them are destroyed by sterilization.

The pyrogens are classified into six groups:

| GROUPS: GRAM NEGATIVE SPECIES | |
|---|---|
| (1) Shigella group: | *S. flexneri* (dysentery) (2 strains) |
| (2) *Serratia marcescens* group | |
| (3) Salmonella group: | *S. abortus equi* |
| | *S. enteritidis* |
| | *S. typhosa* 0901 |
| | *S. typhimurium* |
| (4) *Escherichia coli* group: | *E. coli* 0127:B8 |
| | *E. coli* 055:B5 |
| | *E. coli* 026:B6 |
| | *E. coli* 0111:B4 |
| | *E. coli* 0128:B12 |
| (5) Pseudomonas group | |
| (6) Porteus group | |

Neither the mode(s) of their activity nor their structures are known. However, in general, it is known that in gram-negative bacteria, the glycopeptide basal layer is covered with lipopolysaccharide which constitutes 20–30% of the cell wall. Lipopolysaccharides, components of the whole somatic antigen, with molecular weights of the order of $10^6$ to $10^7$, exhibit endotoxin activity. It is difficult to construct a molecular model for a lipopolysaccharide which would adequately explain the shapes revealed by electron microscopy.

Endotoxins of high antigentic activity have been extracted from bacteria by using one of the recognized published procedures. The best known are the Boivin trichloroacetic acid procedure (Boivin, A., and Mesrobeanie, L., Compt. Rend. Soc. Biol. 113,490, (1933); 128,5 (1938); as modified by Webster, Sagin Landy and Johnson (Webster, M. E., Sagin, J. F., Landy, M. and Johnson, A., J. Immunology, 74, 455 (1955), and the trypsin digestion method of Hartwell and Shear (Hartwell, J. L., and Shear, M. J. J. Nat. Cancer Inst., 4, 107–22, (1943). These methods produce bacterial endotoxins possessing properties adequate for most immunological and pathological studies. The purified endotoxins are comparatively stable in the solid form, but they may become inactivated in solution by hydrolysis.

*Shigella dysenteriae* has been proposed as an international reference bacterium for preparing endotoxins for pyrogenic activity. The endotoxin derived from this source contains 4.5–4.6% nitrogen and 0.80–0.85% phosphorus. It has a molecular weight of about $10^7$ and a strong pyrogenic activity at a level of 0.01 ppm in water (Humphrey, J. H., and Bangham, D. R., Bull Org. Mond. Sante, 20 1241–44 (1959).

The first significant pyrogenic work was done between 1911-1916 by Jona (Jona, J. L., Med. J. of Australia iii, 71–73 (1916) and Hort and Penfield (Hort, E. C., and Penfield, W. J. Britt. Med. J., 2, 1589 (1911). They discovered that introvenous infusions cause elevation of body temperature. In their work freshly prepared distilled water was injected into both a man and animals as a control. A portion of the same distilled water was innoculated into an unsterile container for a period of time and this preparation was then injected into the same man and animals. The febrile reaction occurred only when the innoculated distilled water was injected into the unsterile container. The concluded that the fever-causing product, called pyrogen, was associated with bacteria but was not a part of the bacteria themselves since autoclaving, boiling and filtering did not reverse the febrile reaction. They also were able to classify microorganisms into pyrogenic-type gram negative and nonpyrogenic-type gram positive. Because of the lack of advanced equipment and knowledge their experiments were limited, but they formed the basis for the development of the modern standardized pyrogen test. Siebert (Siebert, F. B., Amer, J. Physiol. 67, 90–04 (1923) and 71, 621–51 (1925), in 1923, confirmed these observations by injecting distilled water into rabbits. In her experiments she demonstrated that bacterial products are present in all pyrogenic fluids that are unaffected by autoclaving, boiling and filtering techniques. She concluded that pyrogenic reactions occur even in sterile fluids and that pyrogenic reactions can be prevented in pharmaceutical preparations only by the removal of pyrogens.

In the conventional method parenteral solutions are examined for pyrogens by using rabbits as test animals according to the procedure outlined in the United States Pharmacopeia (USP). This procedure was adopted in the early 1940's when the need for an official pyrogen test was first recognized. A collaborative study was undertaken by the Food and Drug Administration, the National Institutes of Health, and 14 pharmaceutical manufacturing companies. As a result of these studies, the first official pyrogen test was adopted and appeared in the XIIth Revision of the United States Pharmacopeia. Pharmaceutical companies and research laboratories have made extensive use of the USP rabbit pyrogen test during the past 35 years because of its low cost and the ease with which the rabbits are handled during the test. However other animals such as dogs, cats, monkeys, and horses are equally reliable for the test. The rabbit is reported to be the most sensitive animal for indicating the absence of pyrogens, whereas the dog is the most sensitive animal for establishing the presence of pyrogens. Some investigators have used both animals in order to obtain a better indication, particularly in doubtful cases.

The test is performed in a room in which the temperature and humidity are maintained at the same levels as the room in which the animals are housed.

The rabbit test described in detail in application Ser. No. 745,966 now U.S. Pat. No. 4,093,381 and incorporated herein by reference.

BRIEF DESCRIPTION OF THE INVENTION

An analytical method capable of determining pyrogens at the 10 part per billion level is described in application Ser. No. 745,966 now U.S. Pat. No. 4,093,381. The analytical method of this invention is a substantial improvement over the method of application Ser. No. 745,966 in that it is capable of detecting pyrogens as low as 1 to 5 parts per billion level. The method depends on the measurement of the ultra-violet spectrum of solutions containing the pyrogens over the 200 to 400 nm range using a cell 12 centimeters in length and a cell 14 centimeters in length, and is valid for detecting members of the six groups of pyrogens: Shigella, *Serratia marcescens*, Salmonella, *Escherichia coli*, Pseudomonas, and Porteus.

DETAILED DESCRIPTION OF THE INVENTION

An absorption spectrum is obtained by placing a substance in a suitable cell and exposing it to the energy source of interest in the frequency range being studied. The spectrophotometer is designed so that it measures the transmitted energy relative to the incident energy at a given frequency. The energy required to excite an electron in a compound from its ground state molecular orbital to an excited state is directly proportional to the frequency of the radiation that causes the transition:

$$E_2 - E_1 = h\nu$$

where $E_2$ and $E_1$ are the energies of the initial and final states, respectively, h is Planck's constant, $6.624 \times 10^{-27}$ erg-sec and $\nu$ is the frequency of the incident radiation.

When a molecule absorbs electromagnetic radiation in the ultra-violet or visible region, the electronic transitions are accompanied by the lower-energy vibronic and rotational transitions of the molecule as a whole as well as those of the individual chemical bonds within the molecule. These cause absorption bands to appear in the spectrum.

Such absorption is described by the Beer-Lambert law. Beer's law states that in a non-absorbing solvent, each solute molecule absorbs the same fraction of incident light regardless of the concentration. This law is valid only in dilute solutions. Lambert's law states that the intensity of light passing through a homogeneous medium decreases logarithmically as the thickness of the layer increases. The combined laws may be written:

$$A = \log(lo/l) = \epsilon l c$$

where:
A is the absorbance.
lo is the intensity of incident light.
l is the intensity of transmitted light.
l is the cell thickness in cm.
c is the concentration in mole/liter.
$\epsilon$ is the molar absorptivity or extinction coefficient in liters/mole-cm.

Modern ultra-violet/visible spectrophotometers can commonly measure spectra from 180 nm to 800 nm.

My invention is illustrated by the following specific but non-limiting example.

EXAMPLE

An ACTA MVI Spectrophotometer was used for measuring the absorbance of endotoxin solutions over a concentration range of 0–5 and 5 to 10,000 ppb.

| Endotoxins- | Shigella group - *Serratia marcescens* group | *S. flexneri* (dysentery) (2 strains) |
|---|---|---|
| | Salmonella group | *S. abortus equi* |
| | | *S. enteritidis* |
| | | *S. typhosa* 0901 |
| | | *S. typhimurium* |
| | *Escherichia coli* group - | *E. coli* 0127:B8 |
| | | *E. coli* 055:B5 |
| | Pseudomonas group | *E. coli* 0128:B12 |
| | | *E. coli* 026:B6 |
| | Porteus group | *E. coli* 0111:B4 |

All endotoxins were prepared commercially by the Westphal extraction method and were shipped in powder form in vials that must be kept refrigerated.

Since the endotoxins have low solubilities in water, all stock solutions were prepared at 50 ppm concentrations. The solutions were prepared by dissolving 50 mg of each endotoxin in 1-liter of endotoxin-free distilled water.

Before measuring the endotoxin concentrations it was necessary to establish the wavelength of maximum absorption. It was also necessary to establish that the endotoxin absorption followed Beer's law.

The data in Table 1 shows representative examples of the advantage of the procedures of the instant application over the procedure disclosed in Application Ser. No. 745,966, now U.S. Pat. No. 4,093,381. In this run determinations were made using cells 10-cm, 12-cm, and 14-cm in length. The data shows the substantial improvement in sensitivity when cells 12 and 14 centimeters in length are used.

The measurements were carried out at a temperature of 20° to 30° C. and a pressure of one atmosphere.

The absorption maxima for all individual endotoxins are essentially the same, i.e., 258 nm. For the five endotoxin mixtures, the absorption maxima peak broadened to some extent.

All measurements were made at 258 nm and with a slit width of 0.9 mm with the Beckman sensitive instrument, ACTA MVI.

The settings of the ACTA MVI Spectrophotometer were kept constant throughout the experiment as indicated below:
Scanning Wavelength Range: 300-225 nm
Scanning Speed: ½ nm/sec
Chart Display: 10 nm/inch
Chart Speed: 1 inch/min
Period Set: 1
Span: 0.05
The data collected is set out in Table I.

TABLE I

| SENSITIVITY AND DETECTION LIMIT IMPROVEMENT FOR UV ABSORPTION DATA FOR GROUPS AND SPECIES OF ENDOTOXINS (PYROGENS) MEASURED AT 258nm.** |||||||
|---|---|---|---|---|---|---|
| A. Group or Species of Endotoxin | B. Conc. in ppb* | C. Detection Limit by Cell Length 10 cm | D. Detection Limit by Cell Length 12 cm | E. Detection Limit by Cell Length 14 cm | F. Percent Increase in Sensitivity due to Cell Length From 10 cm to 12 cm | G. Percent Increase in Sensitivity due to Cell Length From 10 cm to 14 cm |
| *E. coli* | | | | | | |
| 0127:B8 | | 0.0010 | 0.0013 | 0.0016 | 30 | 60 |
| 0128:B12 | | 0.0006 | 0.009 | 0.0010 | 50 | 67 |
| 055:B5 | 2 | 0.0004 | 0.0005 | 0.0006 | 25 | 50 |

TABLE I-continued
SENSITIVITY AND DETECTION LIMIT IMPROVEMENT FOR UV ABSORPTION DATA FOR GROUPS AND SPECIES OF ENDOTOXINS (PYROGENS) MEASURED AT 258nm.**

| A. Group or Species of Endotoxin | B. Conc. in ppb* | C. Detection Limit by Cell Length 10 cm | D. Detection Limit by Cell Length 12 cm | E. Detection Limit by Cell Length 14 cm | F. Percent Increase in Sensitivity due to Cell Length From 10 cm to 12 cm | G. Percent Increase in Sensitivity due to Cell Length From 10 cm to 14 cm |
|---|---|---|---|---|---|---|
| S. Typhosa 0901 | | 0.0006 | 0.0007 | 0.0008 | 17 | 33 |
| S. marcescens | | 0.0005 | 0.0007 | 0.0008 | 40 | 60 |
| E. coli | | | | | | |
| 0127:B8 | | 0.0019 | 0.0025 | 0.0037 | 24 | 49 |
| 0128:B12 | | 0.0014 | 0.0019 | 0.0026 | 36 | 86 |
| 055:B5 | 5 | 0.0012 | 0.0015 | 0.0018 | 25 | 50 |
| S. Typhosa 0901 | | 0.0015 | 0.0017 | 0.0019 | 13 | 27 |
| S. marcescens | | 0.0014 | 0.0018 | 0.0021 | 29 | 50 |
| E. coli | | | | | | |
| 0127:B8 | | 0.0033 | 0.0038 | 0.0049 | 15 | 49 |
| 0128:B12 | | 0.0027 | 0.0031 | 0.0046 | 15 | 70 |
| 055:B5 | 10 | 0.0024 | 0.0027 | 0.0032 | 13 | 33 |
| S. Typhosa 0901 | | 0.0030 | 0.0037 | 0.0043 | 23 | 43 |
| S. marcescens | | 0.0029 | 0.0036 | 0.0040 | 24 | 36 |
| E. coli | | | | | | |
| 0127:B8 | | 0.0047 | 0.0059 | 0.0064 | 26 | 36 |
| 0128:B12 | | 0.0040 | 0.0045 | 0.0054 | 13 | 35 |
| 055:B5 | 15 | 0.0036 | 0.0042 | 0.0050 | 17 | 39 |
| S. Typhosa 0901 | | 0.0045 | 0.0053 | 0.0064 | 18 | 42 |
| S. marcescens | | 0.0043 | 0.0054 | 0.0062 | 26 | 44 |
| E. coli | | | | | | |
| 0127:B8 | | 0.0076 | 0.0091 | 0.0107 | 20 | 41 |
| 0128:B12 | | 0.0067 | 0.0079 | 0.0095 | 18 | 42 |
| 055:B5 | 25 | 0.0058 | 0.0072 | 0.0086 | 24 | 48 |
| S. Typhosa 0901 | | 0.0075 | 0.0090 | 0.0098 | 20 | 31 |
| S. marcescens | | 0.0073 | 0.0086 | 0.0105 | 18 | 45 |
| H. Average Percent Increase of 25 Values of Column F & G = | | | | | 23 | 47 |

*ppb = Parts per Billion
**Each Detection Limit Value is an Average of 54 Readings Using the Acta MVI Spectro Photometer

What is claimed is:

1. A process for assaying endotoxins in aqueous liquids at levels as low as 1 to 5 parts per billion comprising the following steps:
   (a) introducing a known volume of the sample into a sample cell having a length of at least 12 centimeters,
   (b) maintaining the temperature of the sample between 20° and 30° C.,
   (c) passing ultra violet radiation of a wave length between 200 and 800 nm thru said liquid sample in the cell,
   (d) measuring the absorbance of the detecting radiation at 258 nm.

2. The method according to claim 1 wherein the cell length is 12 centimeters.

3. The method according to claim 1 wherein the cell length is 14 centimeters.

4. The method according to claim 1 wherein the endotoxins are present in the solution in a concentration of between 1 and 10,000 parts per billion.

5. The process according to claim 1 when the endotoxins are selected from the following groups: Shigella, *Serratia marcescens*, Salmonella, *Escherichia coli*, Pseudomonas and Porteus.

6. A process for detecting endotoxins in aqueous liquids comprising the following steps:
   a. Introducing a known volume of a sample into a sample cell having a length of at least twelve centimeters,
   b. Maintaining the temperature of the sample between 20° and 38° C.,
   c. Passing ultraviolet radiation at a wave length between 200 and 800 nm through said liquid sample in the cell,
   d. Measuring the absorbent of the radiation over the 200 to 400 nm range.

* * * * *